US006503698B1

(12) United States Patent
Dobrinsky et al.

(10) Patent No.: US 6,503,698 B1
(45) Date of Patent: Jan. 7, 2003

(54) CRYOPRESERVATION OF SWINE EMBRYOS

(75) Inventors: John R. Dobrinsky, Beltsville, MD (US); Hiroshi Nagashima, Kawasaki (JP)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/594,704

(22) Filed: Jun. 16, 2000

(51) Int. Cl.$^7$ ................................................. A01N 1/00
(52) U.S. Cl. ........................ 435/1.3; 435/374; 435/378; 435/404; 424/582
(58) Field of Search .......................... 435/1.3, 374, 378, 435/404; 530/853; 600/34; 604/55; 424/582

(56) References Cited

U.S. PATENT DOCUMENTS 5,358,931 A  *  10/1994  Rubinsky et al.

FOREIGN PATENT DOCUMENTS

WO     WO 95/05075     *  2/1995

OTHER PUBLICATIONS

Graves, W., Dissertation Abstracts International, 44(1): 22. Removal of zona pellucidae, development and microsurgery of cleaving domestic animal embryos, 1983.*
Kobayashi et al., Cryobiology, 36: 20–31. Piglets produced by transfer of vitrified porcine embryos after stepwise dilution of cryoprotectants, 1998.*
Nagashima et al., Nature, 374: 416, Cryopreservation of porcine embryos, 1995.*
Dobrinsky, J of Reproduction & Fertility Supplement, 52: 301–312. Cryopreservation of pig embryos, 1997.*
Nagashima, H., et al., "Cryopreservation of Porcine Embryos", *Nature*, vol. 374, p. 416, Mar. 30, 1995.
Dobrinsky, J.R., et al., "Cryopreservation of Porcine Embryos by Vitrification: A Study of In Vitro Development", *Theriogenology*, vol. 42, pp. 25–35, 1994.
Nagashima, H., et al., "Nuclear Transfer of Porcine Embryos Using Cryopreserved Delipated Blastomeres as Donor Nuclei", *Molecular Reprod. and Develop.*, Vol. 48, pp. 339–343, 1997.
Nagashima, H., et al., "Recent Advances in Cryopreservation of Porcine Embryos", *Theriogenology*, vol. 41, pp. 113–118, 1994.
Wilmut, I., "The Low Temperature Preservation of Mammalian Embryos", *J. Reprod. Fert.* vol. 31, pp. 513–514, 1972.
Polge, C., et al., "The Low Temperature Preservation of Cow, Sheep and Pig Embryos", *Cryobiology*, vol. 11, p. 560, 1974.
Polge, C., et al., "Freezing Eggs and Embryos of Farm Animals", *Cryobiology*, vol. 15, pp. 370–373, 1978.
Dobrinsky, J.R., "Cryopreservation of Pig Embryos", *J. Reprod. Fert. Suppl.*, vol. 52, pp. 301–312, 1997.
Rall, W.F., et al., "Ice–Free Cryopreservation of Mouse Embryos at –196°. C by Vitrification", *Nature*, vol. 313, pp. 573–575, 1985.
Kobayashi, S., et al., "Piglets Produced by Transfer of Vitrified Porcine Embryos After Stepwise Dilution of Cryoprotectants", *Cryobiology*, vol. 36, pp. 20–31, 1998.
Dobrinsky, J.R., "Cellular Approach to Cryopreservation of Embryos", *Theriogenology*, vol. 45, pp. 17–26, 1996.
Dobrinsky, J.R., et al., "Cytoskeletal Analysis of Vitrified Porcine Embryos", *J. Anim. Sci.*, Suppl. 1, vol. 72, p. 82, 1994.
Dobrinsky, J.R., "Cryopreservation of Porcine Embryos: Current Status and Perspectives", *Embryo Transfer Newsletter*, vol. 11, No. 4, pp. 13–18, 1993.
Niemann, H., et al., "Manipulating Early Pig Embryos", *J. Reprod. and Fert. Suppl.*, vol. 48, pp. 75–94, 1993.
Dobrinsky, J.R., et al., "Birth of Piglets After Transfer of Embryos Cryopreserved by Cytoskeletal Stabilization and Vitrification", *Biology of Reprod.*, vol. 62, pp. 564–570, 2000.

* cited by examiner

Primary Examiner—Christopher R. Tate
Assistant Examiner—Michele C. Flood
(74) Attorney, Agent, or Firm—M. Howard Silverstein; John D. Fado; Janelle S. Graeter (57) ABSTRACT

A method for the cryopreservation of zona pellucida-intact, early-stage swine embryos, morulae and blastocysts includes centrifuging the embryos prior to cryopreservation in order to remove intracytoplasmic lipids. The lipids are localized external to the embryo proper inside the zona pellucida, thus neutralizing harmful effects which prevent subsequent embryological development. The embryos may be cryopreserved by vitrification or conventional freezing. After recovery and rehydration, zona pellucidae are removed, and intact, viable embryos are transferred to recipient females.

15 Claims, 5 Drawing Sheets

CRYOPRESERVATION OF SWINE EMBRYOS

BACKGROUND OF THE INVENTION

1. Field of the Invention

Cryopreservation methods exist which adequately preserve germplasm and embryos from most livestock. Pig embryos are an exception, however, since whole early stage pig embryos up to the morula stage do not develop after conventional cryopreservation. There has thus been a strong incentive to develop a method which allows effective preservation of embryos from these animals at all stages of embryological development. This invention relates to a method for cryopreservation of swine embryos at the morula/blastocyst stage utilizing vitrification or freezing. The process allows effective, long-term storage of embryos for subsequent transfer to recipient females.

2. Description of the Relevant Art

Boar sperm cryopreservation methods have been available since 1975 and utilized sparingly in commercial production. There has been little success in preserving pig oocytes and embryos by conventional freezing methods, however. The cryopreservation of embryos in addition to sperm thus represents a potential increase in the efficiency of transmitting improved genetic potential.

Pig embryos suffer from severe sensitivity to hypothermia (Wilmut, I. 1972. *J. Reprod. Fertil.* vol. 31, pp. 513–514; Polge et al. 1974. *Cryobiology.* vol. 11, p. 560; Polge and Willadsen. 1978. *Cryobiology.* vol. 15, pp. 370–373; Pollard and Leibo. 1994. *Theriogenology.* vol. 41, pp. 101–106; all herein incorporated by reference) which limits their ability to withstand cryopreservation. A high lipid content is believed to be the critical factor in hypothermic sensitivity and cryosurvival.

While numerous studies have reported on conventional freezing methods, vitrification has more recently shown potential for avoiding the problems associated with cooling sensitivity and ice crystallization (Dobrinsky, J. R. 1998. *J. Reprod. Fert.* suppl. 51, pp. 301–312; Dobrinsky et al. 2000. *Biology of Reproduction.* vol. 62, pp. 564–570; both herein incorporated by reference). Cattle embryos, for example, have been successfully cryopreserved by vitrification (Massip et al. 1986. *Cryo-Letters.* vol. 7, pp. 270–273; Dobrinsky et al. 1991. *Theriogenology.* vol. 35, p. 194; both herein incorporated by reference), and van Wagtendonk-de Leeuw et al. (1997. *Theriogenology.* vol. 48, pp. 1071–1084, herein incorporated by reference) showed that bovine embryo vitrification could be successfully applied under field conditions without a reduction in pregnancy rate. Dobrinsky and Johnson (1994. *Theriogenology.* vol. 42, pp. 25–35, herein incorporated by reference) first demonstrated the efficacy of vitrification of swine embryos where survival and subsequent development in vitro could be established (up to 40% survival). Embryo survival, however, was limited to expanded and early hatched blastocyst stage embryos. It has been shown that hatched blastocyst pig embryos can survive vitrification and, after transfer, can go on to develop in vivo to term (Dobrinsky et al. 1998. *Theriogenology.* vol. 49, p. 166; Kobayashi et al. 1998. *Cryobiology.* vol. 36, pp. 20–31; both herein incorporated by reference). The numbers of recipients in these studies were low, however, and they have not been repeated. Most recently, Dobrinsky et al. (2000, supra) have shown that vitrified hatched blastocyst stage embryos are capable of surviving preservation with the production of live offspring after vitrification, warming and embryo transfer.

Although success with the cryopreservation of hatched blastocysts has been achieved and reported in the literature, embryos preserved at the hatched blastocyst stage of development cannot be utilized globally, fresh or cryopreserved under conventional commercial circumstances. Hatched blastocysts have lost the zona pellucida, or outer layer, by that stage of development, and it is a requirement for the international movement of embryos that they be zona pellucida-intact (*Manual of the International Embryo Transfer Society*, 3rd ed. (1998). The zona pellucida surrounds the embryo from the oocyte to the late blastocyst (hatched blastocyst) stage. During fertilization, it acts as a barrier to polyspermic insemination, allowing only one sperm to penetrate and thus fertilize the oocyte. The matrix also acts as an artifactual barrier to pathogens that may be present in the uterus of the mother. These pathogens may infect the embryo after hatching from the zona pellucida has occurred, thus transporting pathogens from the mother to the embryo which could in turn possibly infect a recipient animal. The search has therefore continued for a method for the effective cryopreservation of swine embryos having intact zona pellucidae.

SUMMARY OF THE INVENTION

We have discovered a novel process for the cryopreservation of swine embryos which is effective at the morula/blastocyst stage of development, at which stage the zona pellucida is intact. The method requires a centrifugation step prior to cryopreservation which allows lipids distributed throughout the embryo to become sufficiently localized that damage during cryopreservation to the embryo caused by the presence of intracellular lipids is thereby avoided. Further, after vitrification and warming or freezing and thawing, as appropriate following cryopreservation, the zona pellucida is removed from the embryo before transfer into a recipient female. The embryos then continue normal development in vivo.

In accordance with this discovery, it is an object of the invention to provide a method for cryopreserving swine embryos having intact zona pellucidae. The cryopreserved embryos may be further processed for embryo transfer to a recipient female.

It is also an object of the invention to provide a cryopreserved swine embryo having an intact zona pellucida which is effective for embryo transfer.

Other objects and advantages of the invention will become readily apparent from the following description.

BRIEF DESCRIPTION OF THE DRAWINGS

FIG. 2 shows pig embryos for cryopreservation: a) morula-stage pig embryos; b) morula-stage pig embryos after centrifugation under the influence of cytoskeletal stabilizer cytochalasin-b, embryo ready for cryopreservation; c) morula-stage pig embryos after cryopreservation by vitrification, warming, cryoprotectant dilution and rehydration in the absence of cytochalasin b; pronase treatment to remove zona pellucida; d) morula-stage pig embryos after zona pellucida removal and 4 hr culture; embryos ready for embryo transfer.

DETAILED DESCRIPTION OF THE INVENTION

Conservation of genetic resources is essential for future availability of desirable genes and germplasm. Banking germplasm from animals having unique genetic, production and disease resistance traits would assist the acquisition, identification and characterization of potentially useful germplasm, ensure genetic variation by the preservation of selected stocks, and facilitate utilization of germplasm in research and industry. An effective cryopreservation method will have a significant impact on the ability to store pig embryos indefinitely.

The transportation and distribution of the best genetic resources would also be enhanced by cryopreservation methods which result in a product meeting the requirements for international transport. Currently, large numbers of live animals are transported by air freight from countries where nucleus herds are located to countries where new breeding units are being established. Transportation costs are extremely high and requirements for health certifications and the associated tests add considerably to the overall cost. Shipping embryos instead of live animals would greatly improve cost containment.

In addition, embryo cryopreservation provides the opportunity to preserve maternal genetic information indefinitely, thus enabling the transmission of improved genetic potential in a form other than a live animal, a first for maternal genetics in swine.

Thus, embryo cryopreservation coupled with embryo transfer is advantageous for swine production. Implementation of methodologies for long-term embryo preservation and transfer would provide a foundation for effective utilization of the world's best genetic resources on a global basis while modernizing pork production and enhancing genetic improvement programs.

Initially, large commercial swine breeders and large farms are expected to utilize the technology for a number of reasons, including transport of maternal germplasm, rapid regeneration or expansion of new or existing lines, extraction or rescue of healthy stock from diseased herds, elimination of quarantine conditions and the provision of a means for the international import/export of potential breeding stock. Further refinements in non-surgical embryo transfer would put embryo cryopreservation and transfer on the farm for producers.

Previous data as well as reports in the literature suggested that zona pellucida-intact swine embryos had little or no survival after cryopreservation. Nagashima et al. (1995. *Nature*. vol. 374, p. 416, herein incorporated by reference) determined that intracellular lipid was associated with cooling or cryo-sensitivity of pig embryos. Studies were carried out where lipid was removed from the embryo (delipation) before cooling or cryopreservation. Over 60% of delipated 8-cell embryos cleaved after chilling to 4° C., whereas all of the controls lysed within 24 h. Fully delipated embryos survived better than partially delipated embryos, and almost 40% developed to the blastocyst stage. Clearly, pig embryos gained some form of tolerance to chilling with a reduction in lipid content.

It was proposed that delipation resulted in changes in the lipid composition of the plasma membranes which in turn may have limited the extent of phase separation and resultant damage during cooling. Delipation procedures were then applied to conventional freezing of 2- to 8-cell embryos. More than half of delipated embryos survived cryopreservation, whether they had been frozen immediately after delipation or after further culture (to determine mitotic competance) prior to freezing; none of the controls survived. Normal piglets were obtained from at least one recipient after both unfrozen and frozen delipated embryos were transferred. This evidence was the first which directly showed that early cleavage stage embryos could survive cryopreservation following delipation and that the loss of cytoplasmic lipid was somehow compensated for later in development. These observations provided a basis for understanding the pig embryo's sensitivity to cooling and cryopreservation.

In further studies of embryo delipation, morula/early blastocyst stage embryos were harvested at day 5 post-insemination, and both in vitro and in vivo survival was recorded after cryopreservation, recovery and culture or transfer. After delipation, conventional freezing, thawing and culture, >90% of delipated, frozen embryos developed to blastocysts. After delipation, vitrification, warming and culture, >65% of delipated, vitrified embryos developed to blastocysts. For controls, 97% of delipated, noncryopreserved embryos and 100% of intact noncryopreserved embryos developed in culture. Conclusive evidence was thus provided that morula/blastocyst stage swine embryos could survive cryopreservation if chilling sensitivity due to the presence of lipid were controlled. After transfer of delipated, frozen-thawed morulae/blastocysts to 7 recipient females, 3 gilts farrowed 14 live and healthy offspring. After transfer of delipated, vitrified-warmed morulae/blastocysts to 4 recipient females, 3 gilts farrowed 13 live and healthy offspring. Conclusive evidence was thus provided that morula/blastocyst stage swine embryos with lipid removed could survive cryopreservation and were viable and developmentally competent after transfer to recipient females.

The Nagashima delipation protocol suffered from one major drawback, however: delipation was achieved by an invasive microsurgical manipulation method which resulted in a disrupted zona pellucida. Studies were therefore carried out to develop a noninvasive method for cryopreservation of zona pellucida-intact, early stage pig embryos, morulae and blastocysts, without using micromanipulation to remove intracytoplasmic lipid. Such a method was necessary in order to provide the long-term preservation needed for global transfer of uterine stage pig embryos. These studies utilized centrifugation to isolate lipid external to the embryo proper inside intact zona pellucida.

In initial studies, embryos were either centrifuged to isolate lipid or not centrifuged to retain intact whole embryos, then cryopreserved by conventional freezing or vitrification. Embryos were recovered from cryopreservation and cultured for 48 h. Non-centrifuged frozen or vitrified morulae/blastocysts did not develop in vitro. Centrifuged/frozen and centrifuged/vitrified embryos showed high rates of survival in vitro after 48 h in culture. Embryos developed to blastocysts, however, they did not continue to hatch in vitro, typical for control embryos cultured for 48 h. When centrifuged/vitrified embryos were warmed and transferred to recipient females, pregnancies were not established. With lipid isolated but undelipated, zona pellucida-intact embryos ceased to develop in vitro and did not develop in vivo. It was suspected that lack of further development occurred due to the toxic effects of the lipid which was localized but remained within the intact zona pellucida.

Further studies were carried out to investigate removal of the zona pellucida after centrifugation and cryopreservation. The zona pellucidae were removed from morula/blastocyst embryos which had been centrifuged, cryopreserved, warmed or thawed, and rehydrated. The embryos were then cultured 48 hr. Centrifuged/frozen zona pellucida-removed morulae/blastocysts developed in culture to expanding blastocysts at a rate of 96%. Centrifuged/vitrified zona pellucida-removed morulae/blastocysts developed in culture to expanding blastocysts at a rate of 84%. Centrifuged/ vitrified zona pellucida-removed embryos were transferred to recipient females. Three gilts farrowed 8, 7 and 4 live and healthy offspring. In a subsequent validation study, 6 of 7 gilts farrowed 42 offspring.

The process thus provides means for the long-term preservation of embryos that can be transported internationally and later successfully transferred to recipient females. Morula/blastocyst stage embryos are ideal for surgical or non-surgical embryo transfer in the pig since these are uterine stage embryos possessing a fully intact zona pellucida which is ideal for aseptic embryo washing and transfer. In addition, the method allows conventional freezing or vitrification at all stages of preimplantation pig embryos from zygotes to hatched blastocysts.

Figure 1:
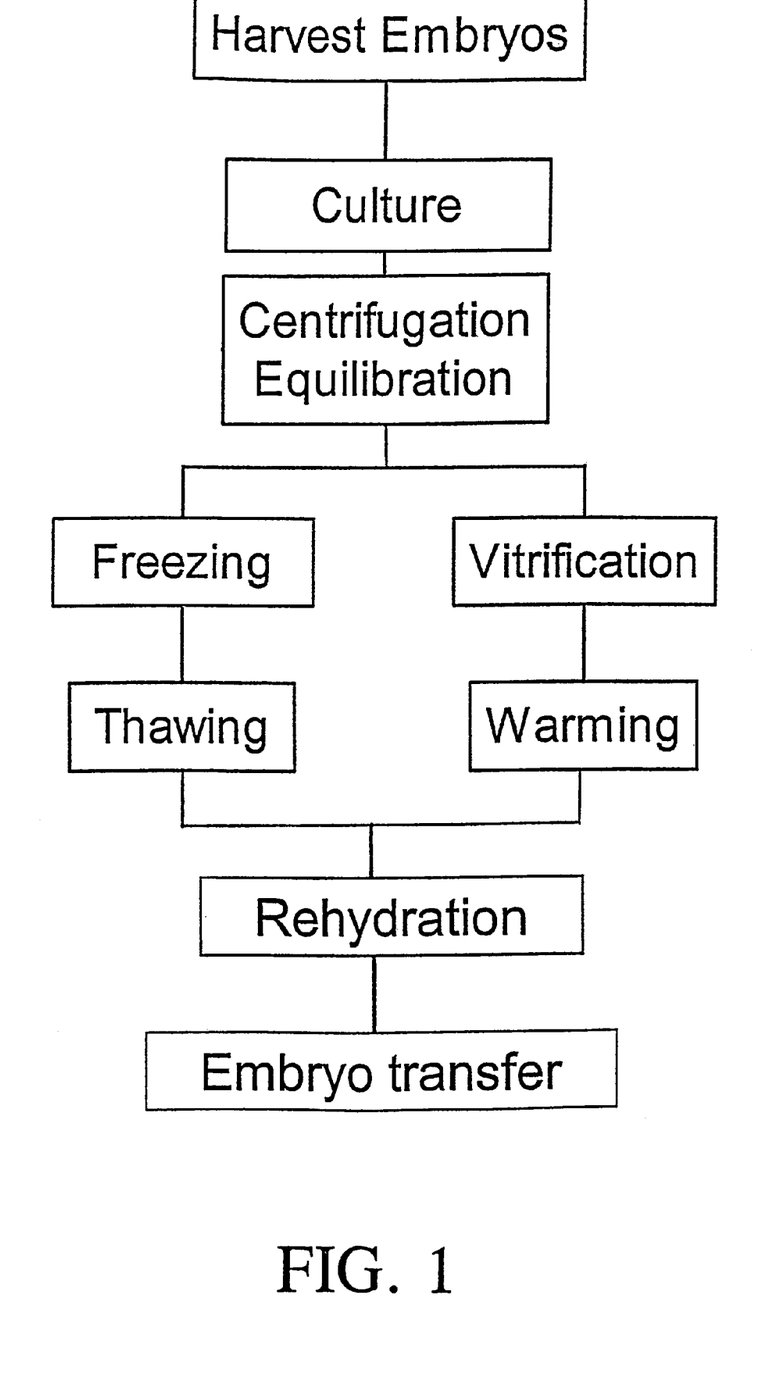
FIG. 1 shows a flow diagram of the cryopreservation process.

The novel process occurs in two stages: cryopreservation and storage, followed by recovery and, subsequently, embryo transfer. Cryopreservation is carried out by providing embryos, culturing the embryos, centrifuging (and equilibrating, as needed), and cryopreserving the centrifuged embryos by either vitrification or freezing. Cryopreserved embryos may be stored indefinitely. Recovery is carried out by warming vitrified or thawing frozen embryos, rehydrating, and removing the zona pellucidae. Recovered embryos are ready for transfer into a recipient female (see FIG. 1 for flow diagram of process).

Embryos may be provided by harvesting from a donor female or obtained by in vitro embryo production procedures, such as in vitro fertilization, embryo cloning or cloning by somatic cell nuclear transfer. These methods are well-known to those of skill in the art. A representative harvesting method is provided in Example 2 and is followed for purposes of discussion herein. While early stage embryos having intact zona pellucidae are of particular interest because of international shipping requirements, the method is also effective for later stage embryos as well as the very early stage zygote.

Embryological development is well-known in the art. Briefly, the zona pellucida is a mucopolysaccharide glycoprotein matrix that surrounds the oocyte, then remains intact to the blastocyst stage. During early cleavage stages (2-, 4-, 8-cell and morula) of embryo development, the zona pellucida remains much as it was at the time of fertilization. At that time, the mature oocyte is one cell of approximately 140 $\mu$m in diameter. After fertilization, the zygote cleaves to form a 2-cell embryo 24–30 hours post fertilization. Within 4–8 hours, the 2-cell embryo cleaves to become a 4-cell embryo, followed by cleavage to the 8-cell stage. The 4–8-cell embryo remains at this stage until late day 4 post-fertilization.

Figure 2A:
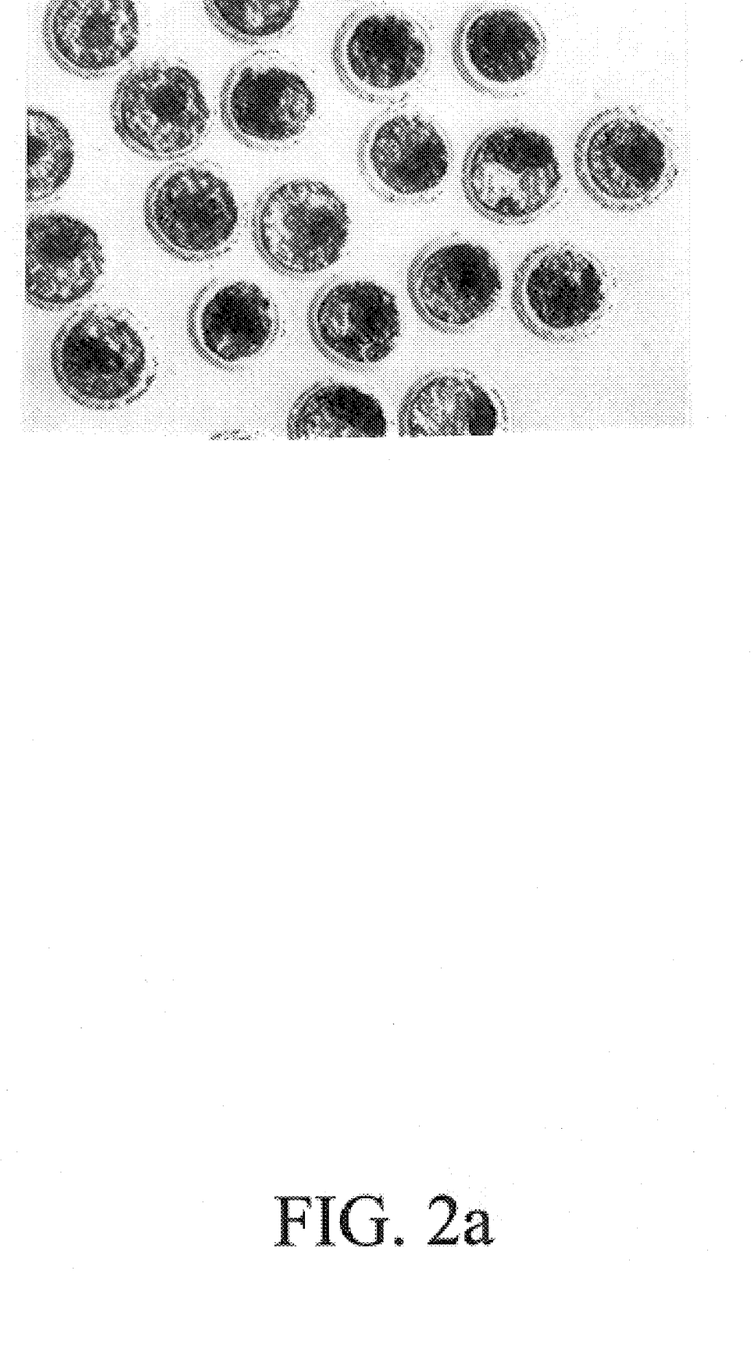

After the 8-cell stage, the embryo undergoes a period of morphological change and cellular differentiation. As mitosis continues, the blastomeres (individual cells) of the 8–16-cell pig embryo begin to compact into the morula, a tight ball of cells, and at day 5 of development, the morula is close to the same diameter as an oocyte. It is a tight ball of 16–32 cells within a fully intact zona pellucida, with tight adherence at adjacent cell-to-cell borders (FIG. 2a). During compaction, individual cells begin to differentiate, with the inner most cells compacting further into a group of differentiated cells known as the inner cell mass (ICM) and the outer most cells continuing to divide to form a trophoblast.

Cellular secretions expel fluid into intercellular spaces to form the blastocoel, a fluid-filled area inside the embryo. At this point (late day 5), the morula differentiates into a blastocyst. As blastocyst development continues through day 6, the blastocoel becomes larger, and the ICM compacts further into two distinct regions of the cell. The blastocoel enlarges and begins to press against the zona pellucida. Upon contact, enzymatic reactions on the plasma membrane of the outermost trophectodermal cells begin to disintegrate the zona pellucida. As the blastocoel enlarges and the zona pellucida thins, the blastocyst enlarges to a 200–225 $\mu$m expanded blastocyst containing 40–60 cells. In vivo, simultaneous effects from the uterine environment also act on the zona pellucida, causing the thinning zona pellucida to eventually break and/or dissolve away, otherwise known as hatching of the blastocyst. The hatched blastocyst is characterized by a vastly increased cell cycle, and, as it enlarges to over 400 $\mu$m, it can contain as many as 2000 cells by day 8 of development.

Thus, one may select an embryo at a particular stage of development by timing the harvesting step according to the timing of ovulation, fertilization and developmental cycle. For example, if one requires a zona pellucida-intact embryo for shipping internationally, one would harvest up through the early part of the expanded blastocyst stage (late day 5–early day 6, estrous=day 0).

Embryos are harvested at about 5–6 days post fertilization. During the harvesting process, embryos are generally placed in medium which is effective in room atmospheric conditions until completion of the process, typically up to approximately 20–30 min.

Following the harvesting step, embryos are cultured under any conditions acceptable for maintaining the viability of the embryo. Conditions of about 39° C., 5% $CO_2$ and air, and about 95% humidity have been found effective. The embryos may remain in culture up to about 2 hr prior to cryopreservation.

Embryos may be stored either vitrified or frozen. Vitrification is the rapid cooling of a viscous, solute concentrated liquid medium in the absence of ice crystal formation. An amorphous glass forms during rapid cooling, usually by direct submersion into liquid nitrogen of a plastic straw containing the embryos in suspension. The glass retains the normal molecular/ionic distributions of a liquid but remains in an extremely viscous, supercooled form (Rall, W. F. 1987. *Cryobiology*. vol. 24, pp. 387–402, herein incorporated by reference). The glass is devoid of all ice crystals, and embryos are not subjected to cellular damage which may be associated with ice crystal formation (Rail and Fahy. 1985. *Nature*. vol. 313, pp. 573–575, herein incorporated by reference).

In the vitrification alternative, subsequent to post-harvest culture, embryos undergo centrifugation and equilibration either separately or simultaneously. For convenience, simultaneous centrifugation and equilibration are preferred (see Example 3). This step achieves permeation and dehydration of the embryo as well as localization of a sufficient amount of its lipid content to neutralize the toxic effects of the lipids during cryopreserved storage. The embryos are placed in vitrification equilibration medium and centrifuged in a microcentrifuge for a time sufficient for lipid to localize outside the embryo within the zona pellucida. Approximately 12–15 min at about 13,000 rpm (microcentrifuge) is generally effective.

Figure 2B:
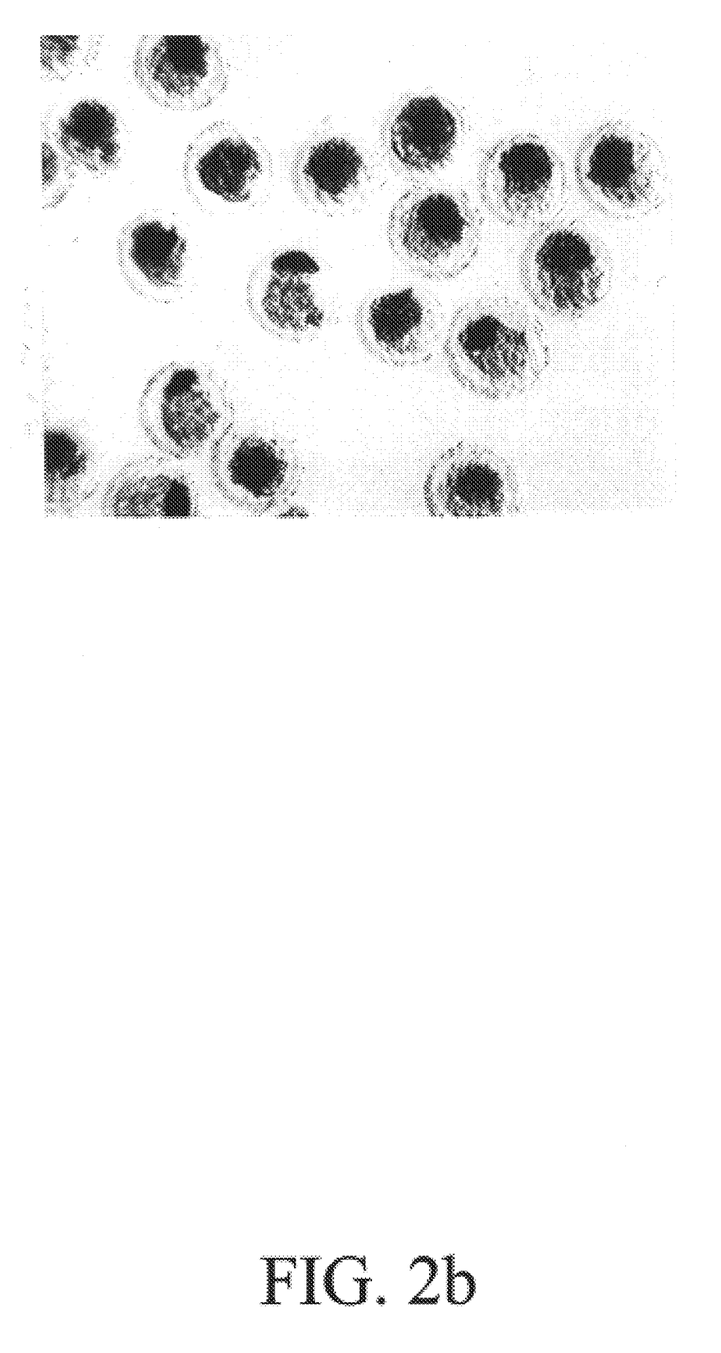

Following centrifugation, embryos are ready for cryopreservation (FIG. 2b). Embryos are washed as previously described in vitrification equilibration medium for about 45 sec, then in vitrification medium for about 1 min, and then loaded into cryopreservation containers in vitrification medium. Containers are appropriately sealed and placed into liquid nitrogen.

In the freezing alternative, lipid is isolated by centrifugation, and embryos are frozen as described by Nagashima et al., supra. After harvesting, embryos are cultured as previously described, i.e. at approximately 39° C., 5% $CO_2$ and air, and about 95% humidity, and may remain in culture up to about 2 hr prior to cryopreservation.

Following culture, embryos are centrifuged in a microcentrifuge for a time sufficient for lipid to localize outside the embryo within the zona pellucida. Approximately 12–15 min at about 13,000 rpm (microcentrifuge) is generally effective. Following centrifugation, embryos are equilibrated in a dehydrating equilibration medium (freezing equilibration medium) about 10 min, then loaded into freezing containers containing freezing medium. A useful freezing procedure is described in Example 4.

Cryopreservation can be extremely disruptive to the cellular organization of embryos (Pollard and Leibo, supra). Ice crystal formation can lyse plasma membranes, storage in liquid nitrogen can disrupt critical intracellular functions and organelles, and the central cytoarchitecture of a cell can be altered or destroyed. Therefore, in both the vitrification and freezing procedures, it is advantageous for at least one cryopretectant and/or stabilizing agent which serves as a means for cytoskeletal and cellular stability to be provided. Useful cryoprotectants are glycerol, propylene glycol and ethylene glycol. The cytoskeletal stabilizer cytochalasin has been found effective for this purpose. Cytochalasin-b (cyto-b) has been found particularly effective and is therefore used for purposes of example herein. Effective concentrations range up to about 10 $\mu$g/ml. Preferred is about 7.5 $\mu$g/ml and is generally considered the standard concentration. Preferably, the procedures are carried out in the presence of these reagents from culture through vitrification or freezing. Appropriate treatments and reagents for the various steps are provided herein. It is advisable that cryoprotectant not be utilized in steps using handling or culture media. In addition, cytoskeletal stabilizer may also be omitted in the equilibration and freezing steps as well as the pre-culture step.

Cyto-b is added to the medium for MF depolymerization. Studies were carried out which documented microfilament (MF) alterations during swine embryo vitrification (Dobrinsky et al. 2000, supra). The ability of cyto-b to stabilize microfilaments during cryopreservation was demonstrated by determining the developmental competence of cytoskeletal stabilized and vitrified pig embryos (Table 1). Vitrified morulae/early blastocysts displayed MF disruptions and lacked developmental competence after cryopreservation while hatched blastocysts displayed variable MF disruption and developmental competence. The presence of cyto-b significantly ($p<0.05$) improved survival and development of expanded and hatched blastocysts.

TABLE 1

Progressive development in vitro of morphologically different stages of swine embryos after cryopreservation by vitrification under the influence of microfilament stabilizer cytochalasin-b.

| | Control | | | + Cytochalasin-b | | |
|---|---|---|---|---|---|---|
| Stage of Development* | n | dev | % dev | n | dev | % dev |
| MB | 17 | 0 | $0^a$ | 17 | 1 | $6^a$ |
| XB | 27 | 6 | $22^{ab}$ | 25 | 15 | $60^{b;z}$ |
| HB1 (<400 $\mu$m) | 36 | 10 | $28^b$ | 48 | 43 | $90^{c;z}$ |
| HB2 (>400 $\mu$m) | 14 | 4 | $29^{ab}$ | 22 | 9 | 41 |

*MB = morulae/early blastocysts; XB = expanded blastocysts; HB1 = hatched blastocysts <400 $\mu$m diameter; HB2 = hatched blastocysts >400 $\mu$m diameter.
[a-c]Values with different superscripts within individual columns are significantly different ($p < 0.05$); analysis of variance for general linearized models, utilizing Waller-Duncan K-ratio T-test. Duncan's Multiple Range Test and Tukey's Tests for embryonic development.
[z]Value with a superscript within individual row is significantly different ($p < 0.01$); Chi-square analysis.

Cyto-b did not appear to improve morula/early blastocyst viability after vitrification in this study; however, the lack of response is believed to be due to the presence of toxic intracellular lipids. The presence of cyto-b in cryopreservation processes for early stage embryos is nevertheless important because it stabilizes the plasma membrane, and in a relaxed state, allows lipids to pass through during centrifugation. With hatched blastocysts, in the presence of cyto-b, the toxic effects of lipids are naturally minimized due to lipid turnover causing a natural reduction of lipid content during continued blastocyst development. Cyto-b in this instance supports the stabilization of the plasma membrane against osmotic shocks during cryopreservation and thus improves survival. In the zona pellucida-intact morula/early blastocyst, however, lipids were trapped inside, therefore the presence of cyto-b, while stabilizing plasma membranes of cells, could not overcome the toxicity of the lipid moiety. In the method of the invention, the presence of cyto-b allows lipids to pass through the membranes of the embryo during centrifugation and equilibration and to localize external to the embryo proper to an extent sufficient to reduce their toxic effects. It has also been shown that pig embryo cytoskeleton can be affected by vitrification and that microfilament depolymerization prior to vitrification improves blastocyst developmental competence after cryopreservation. After transfer, vitrified hatched blastocysts can produce live, healthy piglets that grow normally and, when mature, are of excellent fecundity. After embryo transfer, pregnancy rates of almost 60% were obtained, and litter sizes improved from 5 to 7.25 piglets per litter (Table 2).

TABLE 2

Development of cytoskeletal stabilized and vitrified hatched blastocyst swine embryos after embryo transfer.

| | Embryos | | |
|---|---|---|---|
| Recipient | # ET | # High Quality* | Embryo Development |
| A | 32 | 26 | 10 offspring |
| B | 33 | 27 | open |
| C | 31 | 20 | open |
| D | 31 | 19 | 10 offspring |
| E | 32 | 20 | 6 offspring |
| F | 33 | 16 | open |
| G | 32 | 15 | 3 offspring |
| 7 | 224 | 143 (64%) | 29 offspring (litter average = 7.25) |

*Number of excellent-good embryos at the time of transfer, 3–5 h post-rehydration; remainder of embryos transferred were marginally developing, exhibiting some cellular disruption but maintaining re-cavitation A dehydrating reagent (which may also serve as a cryoprotectant) is included in the vitrification equilibration medium, vitrification medium and freezing medium and also acts as a permeabilizing agent. Effective dehydrating agents are glycerol, propylene glycol and ethylene glycol. The preferred dehydrating agent is glycerol. An effective concentration is about 1.5 M for vitrification equilibration medium and freezing medium, 6.5 M for vitrification medium.

The embryos may be stored indefinitely, and international shipment of the preserved embryos is possible at this point.

Following cryopreservation, and optionally shipment, vitrified embryos are removed from liquid nitrogen and warmed, preferably in a water or alcohol bath, then removed from the cryopreservation container. Although higher temperatures which are consistent with embryo survival may be utilized, room temperature is preferred. They are processed through a cryoprotectant dilution and osmotic rehydration step in order to remove cryoprotectant and cytoskeletal stabilizer and to replace intracellular water lost during the cryopreservation process. First, the embryos are washed at least once in dilution medium, then rehydrated. The embryos may be washed for about 3 min and the step repeated at least once. The embryos remain in rehydration medium for a time sufficient for rehydration to occur, usually about 15 min.

Following cryopreservation, and optionally shipment, frozen embryos are removed from liquid nitrogen and thawed, preferably in a water or alcohol bath. Although higher temperatures consistent with embryo survival may be used, room temperature is preferred. After thawing, the embryos are removed from the freezing container for dilution of cryoprotectant and stabilizing agent, if necessary, and rehydration, i.e. replacement of cellular fluids. A step-wise process is recommended in order to gradually increase osmotic pressure within the cells, thus reducing the chance of embryo rupture: the embryos are first treated for about 10 min with a first rehydration medium, for about 5 min with a second and finally for about 10 min with a third. The embryos may be washed up to 2 times in the same medium, then allowed to rehydrate for about 15 min.

Figure 2C:
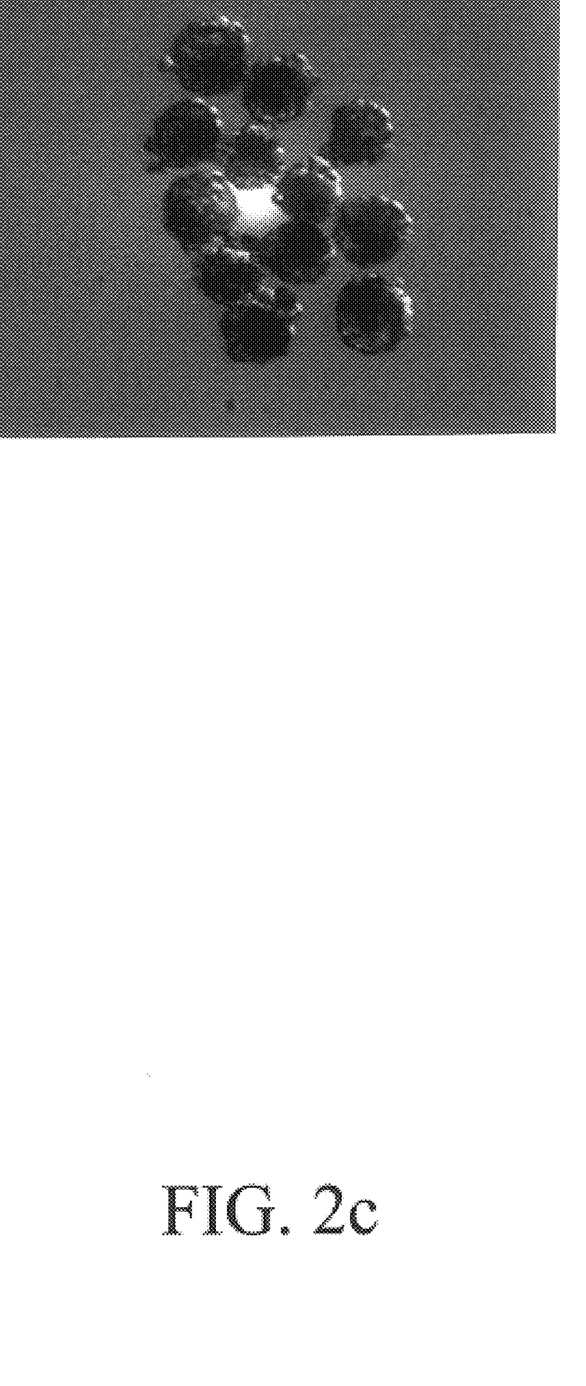

After cryopreservation, dilution and rehydration, the zona pellucida is removed (FIG. 2c). Removal may be accomplished by treatment with a proteolytic enzyme, acidified culture medium or by mechanical removal. Enzymatic removal is preferred, with protease (or pronase) being the preferred enzyme utilized.

Embryos are placed in Dulbecco's phosphate buffered saline (DPBS) containing pronase for up to about 1 min or until the zona pellucida is completely dissolved. Embryos are quickly removed from pronase into handling medium and washed to remove all pronase, about 3 times being generally sufficient. Pronase at a concentration of about 0.5% in DPBS has been found effective.

Figure 2D:
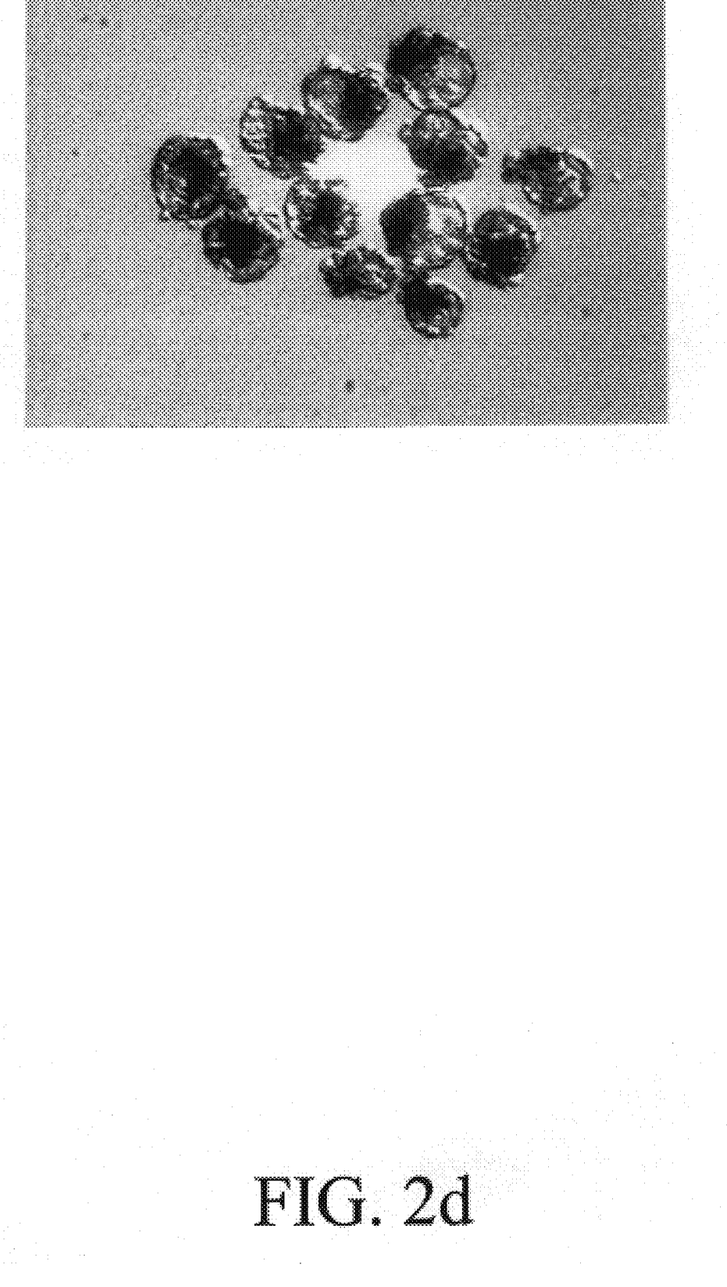

Following zona pellucida removal, the zona-free embryos are placed into culture medium in order to allow repolymerization and cellular stabilization to occur prior to embryo transfer to recipient females (FIG. 2d). They may remain in culture up to about 5 hrs.

Alternatively, after cryopreservation, dilution and rehydration, the embryos are placed into culture medium in order to allow repolymerization and cellular stabilization to occur. Prior to embryo transfer, zona pellucida removal may be carried out as described above.

The transfer of embryos to recipient females is a technique well-known to those of skill in the veterinary arts. The process is well-documented in the literature, and a representative description may be found in Dobrinsky et al., 2000, supra, or Dobrinsky, 1998, supra. In addition, antiprostaglandins were also administered prior to surgical embryo transfer to recipient females at standard recommended veterinary dosages in order to help establish and maintain pregnancy.

Media and reagents useful for the novel process are known in the art and reported in the literature. They are selected according to the particular purpose served. Useful media and reagents for the individual steps of the process are indicated in Table 3, however, it is understood that effective substitutes may also be utilized. Formulations immediately follow (Tables 4, 5 and 6).

Developmental appraisals of the centrifuged cryopreserved embryos were carried out both in vitro and in vivo. For in vitro studies, morulae/blastocysts were cultured for 72 hours post-treatment. After culture, embryos were morphologically evaluated for their developmental progression. Embryos that had cavitated with distinct differentiation of cells into trophectoderm and inner cell mass, and possessed a normal or thinning zona pellucida, were considered to be developed blastocysts or expanded blastocysts, respectively. Those blastocysts that possessed cells extruding through a ruptured zona pellucida or without a zona pellucida at all and exhibited a normal or expanding blastocoelic cavity were considered hatched blastocysts. Since all morulae would have to develop into

TABLE 3

Reagents and Media Useful for Cryopreservation Process.

| | Step/Medium* | Cyto-b | Vitrification | Freezing |
|---|---|---|---|---|
| A. | Post-harvest handling/HM | | + | + |
| B. | Post-harvest culture/CM | | + | + |
| C. | Cyto-b culture/CM | + | + | + |
| D. | Centrifugation and equilibration/EM | + | + | |
| E. | Vitrification/VM | + | + | |
| F. | Centrifugation/HM | + | | + |
| G. | Equilibration/FM | +/− | | + |
| H. | Freezing/FM | +/− | | + |
| I. | Cryoprotectant dilution/DM | | + | + |
| J. | Rehydration/HM | | + | + |
| K. | Zona pellucida (z.p.) removal/RM | | + | + |
| L. | Washing (z.p. removal)/HM | | + | + |
| M. | Culture/CM | | + | + |
| N. | Embryo transfer/HM | | + | + |

*HM = Handling medium; CM = Culture medium; EM = Equilibration medium; VM = Vitrification medium; FM = Freezing medium; DM = Dilution medium; RM = Removal medium.

TABLE 4

Handling Medium (HM) Formulation.

| Compound | Formula Weight | mM | g/l |
|---|---|---|---|
| NaCl | 58.44 | 138.00 | 8.06 |
| KCl | 74.55 | 3.10 | 0.24 |
| $MgCl_2 \cdot 6H_2O$ | 203.30 | 0.50 | 0.10 |
| $CaCl_2 \cdot 2H_2O$ | 147.00 | 2.00 | 0.29 |
| $NaHCO_3$ | 84.01 | 2.00 | 0.17 |
| Hepes Buffer | 238.30 | 10.00 | 2.40 |
| Glucose | 180.20 | 5.50 | 1.00 |
| EDTA | 292.00 | <0.01 | 0.003 |
| BSA-V | — | — | 3.00 |
| Phenol Red | — | — | ≦0.001 |

TABLE 5

Media for Equilibration (EM), Vitrification (VM), Freezing (FM), and Dilution (DM) Steps.

| | % BSA | Glycerol | M |
|---|---|---|---|
| Equilibration medium (EM) | 6 | 14.96 g in 100 ml HM* | 1.5 M glycerol |
| Vitrification medium (VM) | 6 | 59.86 g in 100 ml HM* | 6.5 M glycerol |
| Freezing medium (FM) | — | — | 1.5 M propylene glycol, 0.1 M sucrose in DPBS** |
| Dilution medium (DM)/F | — | — | See Example 4. |
| Dilution medium (DM)/V | — | — | 1 M sucrose in HM* |

*HM = Handling medium.
**DPBS = Dulbecco's phosphate buffered saline.

TABLE 6

Culture Medium (CM) Formulation.[1]

| Compound | Formula Weight | mM | g/l |
|---|---|---|---|
| NaCl | 58.44 | 94.59 | 5.54 |
| KCl | 74.55 | 6.00 | 0.45 |
| $MgSO_4 \cdot 7H_2O$ | 246.50 | 1.19 | 0.29 |
| $CaCl_2 \cdot 2H_2O$ | 147.00 | 1.71 | 0.25 |
| $NaHCO_3$ | 84.01 | 25.07 | 2.11 |
| Phenol Red | — | — | ≦0.001 |
| Glucose | 180.20 | 5.56 | 1.00 |
| Na Pyruvate | 110.0 | 0.33 | 0.04 |
| L-Glutamine | 146.10 | 1.00 | 0.15 |
| BSA-V | — | 12 mg/ml | 12.00 |
| Na Lactate (60% syrup) | 112.10 | 23.00 | 3.35 ml |
| MEM Non-essential amino acids | — | — | 10 ml |
| BME Essential amino acids | — | — | 20 ml |

[1]Dobrinsky et al. 1996. Biol. Reprod. vol. 55, pp. 1069–1074, herein incorporated by reference.

blastocysts within 24 hr following vitrification, those that did were considered as survived and developing in vitro. Morulae that were lysed (verified by propidium iodide staining) or did not develop into blastocysts were considered as not surviving treatment and did not develop in vitro. Results are shown in Table 7. For centrifuged frozen embryos, 96% developed into blastocysts, while 84% of centrifuged vitrified embryos developed normally.

For developmental appraisal in vivo, embryos were placed into culture for 3–5 hrs. Only embryos which were intact or early cavitating with advanced development were considered viable and, after morphological evaluation, were transferred by transoviductal uterine catheterization to asynchronous (−24 h) surrogate gilts. Recipients were checked by boar daily for manifestation of estrous. Recipients that did not return to estrous were allowed to carry the pregnancy to term, while recipients that returned to estrous two consecutive estrous cycles of normal length were considered open or not pregnant. Results are shown in Table 8. Of 11 recipients, 9 were pregnant, producing a total of 61 live offspring (7/litter).

All statistics were determined by analysis of variance for general linearized models (ANOVA/GLM, Duncan/Waller Test, further verified with Tukey's Test) with the aid of a SAS statistical software package (Statistical Analysis System, SAS 6.12, SAS Inst. Inc., Cary, N.C.).

TABLE 7

Survival of porcine blastocysts cryopreserved after centrifugation.

| Centrifugation | Cryopreservation | No. of embryos cultured | No. of embryos developed after cryopreservation (%) | Cell numbers in blastocysts |
|---|---|---|---|---|
| + | Frozen | 25 | 24(96.0)[a] | 100.3 ± 16.2[a] |
| − | Frozen | 22 | 4(18.2)[b] | 64.3 ± 17.2[b] |
| + | Vitrified | 25 | 21(84.0)[a] | 115.4 ± 14.0[a] |
| − | Vitrified | 26 | 2(7.7)[b] | 60.0 ± 4.0[b] |
| + | — | 20 | 20(100)[a] | 216.6 ± 13.4[c] |

[a,b,c]Values with different superscript within columns differ significantly ($P < 0.05$).

TABLE 8

Development of centrifuged, cytoskeletal stabilized and vitrified morula stage swine embryos after embryo transfer.

| | | Litter Size | |
|---|---|---|---|
| Recipient | Status | Live | Total |
| A | Open | — | — |
| B | Pregnant | 8 | 8 |
| C | Pregnant | 7 | 7 |
| D | Pregnant | 4 | 5 |
| E | Open | — | — |
| F | Pregnant | 9 | 10 |
| G | Pregnant | 7 | 7 |
| H | Pregnant | 7 | 8 |
| I | Pregnant | 4 | 5 |
| J | Pregnant | 8 | 8 |
| K | Pregnant | 7 | 7 |
| 11 | 9 (82%) | 61(Live) | 65(Total) |

The following examples are intended only to further illustrate the invention and are not intended to limit the scope of the invention as defined by the claims.

EXAMPLES

Example 1

Experimental Design

Pig morulae/early blastocysts were centrifuged/equilibrated, and then cryopreserved by freezing or vitrification in the presence of the microfilament inhibitor, cyto-b. After cryopreservation, embryos were diluted/rehydrated in the absence of cyto-b. Embryos were placed into standard culture medium (Dobrinsky et al., 1996, supra) to monitor post-thaw developmental competence in vitro or surgically transferred via transoviductal uterine catherization into asynchronous (−24 h; day 4) surrogate females. Embryos were cultured for 48 hours and evaluated, while transferred embryos were allowed to go to term of pregnancy.

Example 2

Embryo Harvesting and Culture

Embryos were produced from natural, normal estrous cycle crossbred gilts that were 6 months of age or older and weighed at least 100 kg at the time of use. All gilts were superovulated and then artificially inseminated twice during the period of standing estrous (~24 hr) with freshly collected and pooled semen that was diluted in Beltsville-TS (BTS, Johnson et al. 1988. Zuchthyg. vol. 23, pp. 49–55, herein incorporated by reference) to a concentration of $\geq 5 \times 10^9$ spermatozoa for each 80-ml dose. Gilts were slaughtered five to seven days after onset of estrous (AI=day 0). Reproductive tracts were excised from the gilts within 3–5 min of slaughter, maintained at 39° C. and transported to the laboratory. The tracts were prepared for flushing by trimming the oviducts and uteri away from the connective tissue while maintaining tissue temperature at 39° C. Embryos were recovered by flushing the excised oviducts and uterine horns with warm (39° C.), sterile handling medium. Only those embryos recovered from gilts slaughtered on day 5 that were late morulae/early blastocysts (MB) and graded excellent or good for developmental stage and morphological appearance were used. Following recovery, all embryos were randomly distributed. Embryos were cultured in NUNC(#176740; Denmark) 4-well tissue culture plates, 500

μl/well culture medium, 10% FBS (no BSA-V present), with the inner reservoir filled with 2 ml culture medium, 10% FBS. For long-term culture, embryos were washed three-four times in the inner reservoir in three-four distinct and separate locations, then washed once each in three of the wells, then placed into the fourth and final well to reside in culture. Embryos were cultured at 39° C. in 5% $CO_2$ in humidified air throughout the study. MB were cultured for 72 hr post-treatment in vitro.

Example 3

Embryo Preservation by Vitrification

Embryos were vitrified as described by Dobrinsky and Johnson (supra) in vitrification medium [6.5M glycerol, 6% bovine serum albumin-V (BSA-V; Sigma Chemical Co., St. Louis, Mo.)]. Prior to cryopreservation, for microfilament depolymerization, embryos were incubated at 39° C. in 5% $CO_2$ and air, 95% humidity for 30–45 min in culture medium containing 7.5 μg/ml cyto-b (Sigma Chemical co., supra; stock=5 mg/ml 95% food grade EtOH). Following incubation in cyto-b, embryos were removed from culture and washed 3 times in 2 ml handling medium with cyto-b for 5 min and then equilibrated in 1 ml handling medium containing 6% BSA-V and cyto-b for 5 min. Embryos were then washed in vitrification equilibration medium (25% glycerol v/v, 6% BSA-V) containing cyto-b, then placed in 20 μl of vitrification equilibration medium containing cyto-b in a 1.5-ml microcentrifuge tube. The tube was placed and counterbalanced in an Eppendorf 5415 microcentrifuge and centrifuged for 13 min at 13,000 rpm. During centrifugation, embryos were dehydrated and equilibrated with glycerol. Total time in vitrification equilibration medium was about 20 min, including the centrifugation time.

Following centrifugation, embryos were vitrified in the presence of cyto-b. Embryos were washed in a 1:1 mixture of vitrification equilibration medium and vitrification medium containing cyto-b for 30–45 sec, washed again in 100% vitrification medium with cyto-b for 30–45 sec, and then placed in prepared 0.25-ml straws for cryopreservation containing 100% vitrification medium with cyto-b. Straws were heat-sealed and placed into liquid nitrogen storage.

Following indefinite cryopreserved storage in liquid nitrogen, embryos were warmed at 25° C. in a water or alcohol bath, then processed through dilution in dilution medium and rehydration in handling medium without cyto-b, to wash and remove cryoprotective agent and cytoskeletal stabilizer from the embryos during osmotic rehydration. Embryos were expelled from straws, then placed into 3 ml dilution medium for 3 min at 39° C., followed by another wash in 1 ml dilution medium for 4 min at 25° C. to continue dilution. After dilution, embryos were washed 3 times and rehydrated in handling medium for 15 min.

Following rehydration, embryos were placed into 0.5% pronase (P5147 protease; Sigma Chemical Co., supra) in DPBS for up to a minute or until zona pellucidae were completely dissolved. Embryos were promptly removed from pronase into handling medium and washed three times as described. Following zona pellucida removal, the lipid-isolated, zona-free morulae were placed into culture for 3–5 hr prior to transfer to recipient females.

Example 4

Embryo Preservation by Freezing

Embryos were lipid isolated by centrifugation and conventionally frozen as described by Nagashima et al., supra in freezing medium. After harvesting, embryos were incubated at 39° C. in 5% $CO_2$ and air, 95% humidity, for up to 45 min in culture medium containing cyto-b. Following incubation in cyto-b, embryos were placed in a 1.5-ml microcentrifuge tube containing 20 μl DPBS with 10% fetal calf serum (FCS) and cyto-b. The tube was placed (counterbalanced) in an Eppendorf 5415 microcentrifuge and centrifuged for 13 min at 13,000 rpm for isolation of cytoplasmic lipid by centrifugation. Embryos were equilibrated in 1.5M propylene glycol for 10 min, and then loaded into 0.25 ml plastic straws with the freezing medium. Straws were heat-sealed and placed into cryopreservation. Embryos were cooled directly from room temperature to −7° C., seeded to induce ice nucleation and held at −7° C. for 10 min, then cooled at a rate of 0.5° C./min to −30° C. using a programmable freezer before placing into liquid nitrogen.

After thawing in a room temperature water or alcohol bath, embryos expelled from straws were rehydrated by exposing them step-wise for 10 min to 0.75M propylene glycol with 0.2M sucrose, for 5 min to 0.2M sucrose, and for 10 min to DPBS with 10% FCS and washing with the same medium 2 times and allowing to rehydrate for 15 min. Following rehydration, embryos were placed into 0.5% pronase in DPBS for up to a minute or until zona pellucidae were completely dissolved. Embryos were promptly removed from pronase into handling medium and washed 3 times as described in Example 3. Following zona pellucida removal, the zona-free embryos were placed into culture for 3–5 hr prior to transfer to surrogate females as previously described.

We claim:

1. A process for the cryopreservation and recovery of swine embryos having intact zona pellucidae comprising providing swine embryos, culturing said embryos, centrifuging the cultured embryos, equilibrating the centrifuged embryos, cryopreserving the centrifuged and equilibrated embryos by vitrification or freezing, storing the cryopreserved embryos, and recovering the cryopreserved embryos having intact zona pellucidae, wherein said recovery process comprises warming vitrified embryos or thawing frozen embryos, rehydrating the embryos and removing the zona pellucidae of rehydrated embryos.

2. The process of claim 1, where said culturing, centrifuging, equilibrating, cryopreserving and storing the embryos is carried out in the presence of at least one cryoprotectant agent and/or cytoskeletal and cellular stabilizing agent, and wherein the concentration of said agent is diluted in warmed or thawed embryos during the recovery process.

3. The process of claim 2, wherein said cytoskeletal and cellular stabilizing agent is cytochalasin.

4. The process of claim 3, wherein said cytochalasin is cytochalasin-b.

5. The vitrification process of claim 1, wherein said centrifugation and equilibration occur simultaneously.

6. The process of claim 5, wherein centrifugation and equilibration are carried out for an amount of time effective for a sufficient amount of lipids present in embryos to localize outside an embryo within the zona pellucida such that toxic effects of the lipids are neutralized during cryopreservation and storage, and for dehydration of embryos.

7. The freezing process of claim 1, wherein said centrifugation is carried out for an amount of time effective for a sufficient amount of lipids present in embryos to localize outside an embryo within the zona pellucida such that toxic effects of the lipids are neutralized during cryopreservation and storage, followed by equilibration effective for dehydration of embryos.

8. The process of claim 1, wherein said warming or thawing is carried out in a water or alcohol bath.

9. The process of claim 8, wherein said warming or thawing in said water or alcohol bath is carried out at room temperature.

10. The process of claim 2, wherein said diluting and rehydrating is carried out sufficient for replacing intracellular fluid lost during dehydration.

11. The process of claim 1, wherein zona pellucidae are removed by treatment with a proteolytic enzyme or acidified culture medium or by mechanical removal.

12. The process of claim 1, wherein the zona pellucidae are removed by treatment with a proteolytic enzyme.

13. The process of claim 12, wherein the proteolytic enzyme is protease or pronase.

14. The process of claim 1, wherein, after removal of the zona pellucidae, embryos are cultured for a time sufficient to allow cytoskeletal repolymerization and cellular stabilization to occur.

15. A cryopreserved swine embryo effective for embryo transfer prepared according to the process of any of claims 1, 2–7, or 8–14.

* * * * *